United States Patent [19]

Cuatrecasas et al.

[11] 4,411,832

[45] * Oct. 25, 1983

[54] POLYSACCHARIDE MATRICES COMPRISING MACROMOLECULAR SPACER ARMS FOR USE AS ADSORBENTS IN AFFINITY CHROMATOGRAPHY TECHNIQUES

[76] Inventors: Pedro Cuatrecasas, 10 Hillside Rd.; Indu Parikh, 4404 Keswick Rd., both of Baltimore, Md. 21210

[*] Notice: The portion of the term of this patent subsequent to Sep. 30, 1997, has been disclaimed.

[21] Appl. No.: 286,763

[22] Filed: Jul. 27, 1981

Related U.S. Application Data

[63] Continuation of Ser. No. 97,889, Nov. 26, 1979, abandoned, which is a continuation of Ser. No. 6,175, Jan. 24, 1979, abandoned, which is a continuation of Ser. No. 876,126, Feb. 8, 1978, abandoned, which is a continuation of Ser. No. 713,108, Aug. 10, 1976, abandoned, which is a continuation of Ser. No. 475,314, May 31, 1974, abandoned.

[51] Int. Cl.³ .............................................. C07G 7/00
[52] U.S. Cl. ................................ 260/121; 260/112 R; 424/177; 424/178; 536/55.1
[58] Field of Search ................. 260/121, 112; 536/18; 424/177, 180

[56] References Cited

U.S. PATENT DOCUMENTS

3,278,392  10/1966  Patchornik ........................... 195/63
3,873,514   3/1975  Chu et al. ............................ 210/31 C
4,225,487   9/1980  Cuatrecasas et al. ............... 260/121

OTHER PUBLICATIONS

Science, 179, pp. 1142–1144, "Biological Activity of Insulin-Sepharose", Cuatrecasas.
Chem. Absts., vol. 79, (1973), 75505h, Wilchek, "Stable and High-Sepharose-Affinity Chromatography".
Journal of Biological Chemistry, 248, No. 18, Sica et al., (3/19/73), pp. 6543–6558.

*Primary Examiner*—John Kight, III
*Assistant Examiner*—Amelia B. Yarbrough
*Attorney, Agent, or Firm*—Burns, Doane, Swecker & Mathis

[57] ABSTRACT

Polysaccharide matrices, including polyfunctional macromolecular spacer "arms" coupled to the backbones of such matrices in multipoint attachment, are useful as adsorbents in affinity chromatography techniques to "separate" the matrix from the specific liquid being chromatographed. Exemplary preferred polyfunctional macromolecules include [1] poly-L-lysine, [2] the graft copolymer, poly(L-lysyl-DL-alanine), [3] native albumin and [4] denatured albumin.

25 Claims, No Drawings

POLYSACCHARIDE MATRICES COMPRISING MACROMOLECULAR SPACER ARMS FOR USE AS ADSORBENTS IN AFFINITY CHROMATOGRAPHY TECHNIQUES

This application is a continuation of application Ser. No. 97,889, filed Nov. 26, 1979, now abandoned, itself a continuation of Ser. No. 6,175, filed Jan. 24, 1979, in turn a continuation of Ser. No. 876,126, filed Feb. 8, 1978, which in turn is a continuation of Ser. No. 713,108, filed Aug. 10, 1976, which in turn is a continuation of Ser. No. 475,314, filed May 31, 1974, all now abandoned.

BACKGROUND OF THE INVENTION

1. Field of the Invention

The present invention relates to certain adsorbents (matrices) for use in affinity chromatography techniques, for example, in the purification of various biologically active molecules such as ligands, proteins, hormones, nucleotides and nucleosides, and more especially, relates to the use of soluble polyfunctional "macromolecular" spacers or "arms" to separate a polysaccharide matrix from the specific ligand or protein to be, e.g., purified. Since "macromolecules" such as the graft copolymer of lysine [backbone] and alanine [side chains] can attach to polysaccharide matrices (for example, cellulose, starch and cross-linked polysaccharide gels such as agarose, Sepharose and Sephadex] at multiple points, the overall chemical stability of the bonding of such polymer to the, e.g., gel, and therefore of other substituents coupled to the polymer, is greatly enhanced.

2. Description of the Prior Art

Affinity chromatography has recently been introduced as a method for purification of biologically active compounds. Cuatrecasas et al, *Proc. Matl. Acad. Sci. U.S.*, 61, 636 (1968). The selective isolation and purification of enzymes and other biologically important macromolecules by "affinity chromatography" exploits the unique biological property of these proteins to bind ligands specifically and reversibly. For example, protein to be purified is passed through a column containing an insoluble polymer or gel to which a specific competitive inhibitor or ligand has been covalently attached. Proteins not exhibiting appreciable affinity for the ligand will pass unretarded through the column, whereas those which recognize the inhibitor will be retarded to an extent related to the affinity constant under the experimental conditions. This method is related in principle to the use of "immunoadsorbents" for the purification of antibodies, which principles have also been applied to the purification of nucleotides, complementary strands of nucleic acids, certain species of transfer RMA, and enzymes by utilization principally of hydrophobic polystyrene or hydrophilic cellulose polymers for the insoluble supporting matrix. Thus, the method depends on the affinity of a protein toward its specific hapten or inhibitor, covalently coupled to an insoluble matrix. In order to use this method successfully, the essential group for interaction with the molecules to be purified must be sufficiently distant from the polymer surface to minimize steric interference. Such a distance can be obtained by introducing a spacer molecule between the solid matrix and the molecule bound thereto. Since the only truly effective method available for binding various molecules to the conventional matrices, e.g., agarose or Sepharose, is by the activation thereof with cyanogen bromide (Axen et al, *Nature* 214, 1302 (1967); Porath et al, *Nature*, 215, 1491 (1967)], the spacer must contain a free amino group through which the binding is effected.

Several different approaches of introducing the spacer have been used. One has been suggested by Cuatracasas et al at *J. Biol. Chem.*, 245, 3059, (1970), using amino alkyl-Sepharose as a starting material. The amino derivative was then reacted with different functional groups, to which ligands were coupled and used for protein purification. All of these derivatives have strong ion-exchange properties due to incomplete coupling of the ligand to the amino or carboxyl groups of succinylated derivatives. Alternative approaches have been suggested. Compare Wilchek et al, *Israel J. Chem.*, 8, 172 (1970) and Wilchek, *FEBS Letters*, 33, 70 (June, 1973).

It has also been recognized that ligands attached to agarose by the CNBr activation reaction [directly or through a spacer arm] are slowly released from the matrix into the buffer medium. Ludens et al, *J. Biol. Chem.*, 247, 7533 (1972); Sica et al, *Nature (London) New Biol.*, 244, 36 (1973). The quantity of ligand released [leakage or bleeding] depends on the temperature and on the specific buffer. Such leakage of the bound ligand from the gel may interfere seriously with affinity chromatographic procedures.

Compare also application, Ser. No. 475,305, filed May 31, 1974, now U.S. Pat. No. 3,947,352, and hereby expressly incorporated by reference.

SUMMARY OF THE INVENTION

It is thus a primary object of this invention to eliminate the foregoing leakage phenomenon, albeit consistent with the aforesaid "steric interference" limitations.

According to the invention, an important approach to the resolution of the noted problem involves the use, as "anchoring" reagents, of a variety of water-soluble polyfunctional polymers which contain large numbers of reactive, e.g., primary amino, groups. By the proper selection of reaction conditions it is possible to couple the polyfunctional polymers so as to achieve multipoint attachment of the polymer to the backbone of a polysaccharide, e.g., agarose, matrix with resultant increased chemical stability. The probability of spontaneous release of the ligand bound to the $NaIO_4$— or CHBr-activated agarose decreases geometrically with the number of attachment points. For example, if alanine is released with a probability of one part per thousand [0.1%], a ligand attached [by the same chemical means] at two points might be expected to be released with a probability of one part per million [0.0001%].

In addition to increasing the chemical stability of the ligand-agarose complex, these polyfunctional spacer arms offer other advantages in affinity chromatography. The macromolecular spacers provide appreciably greater separations of ligand from the matrix backbone [in the order of 150 Å than can be achieved with the conventional spacers available. Furthermore, these polymers exhibit minimal hydrophobicity, and the immediate microenvironment created in the vicinity of the ligands or proteins substituted on such polyfunctional spacer arms appears to be especially favorable in many types of interactions encountered in affinity chromatography. For example, estradiol derivatives of albumin-agarose display much greater affinity for uterine estrogen receptors than do comparable derivatives containing conventional spacers [15-25 Å in length]. Sica et al, supra. Similarly, leukocytes interact much better with agarose beads containing histamine and catecholamines attached to the beads through albumin spacers. Weinstein et al., *J. Clin. Invest.*, 52, 1349 (1973).

Some of the biospecific adsorbents prepared with the use of polyfunctional spacer arms are so effective that significant extraction of cholera toxin occurs even when the gels are diluted 200- to 600-fold with unsubstituted agarose. Adsorbents diluted in this fashion can often be used routinely for the purification of estrogen and insulin receptors by affinity chromatography, since selective adsorption of receptors in excess of 90% can still be achieved in the instances tested. An important consequence of the procedures which use such diluted adsorbents is that the leakage of ligand from the gel is drastically reduced, thus minimizing the complications that can result from such leakage during chromatography of the sample. Furthermore, by diluting the agarose adsorbent with unsubstituted agarose, the possible complications or difficulties encountered in the thorough washing of the gel before use are reduced, and the nonspecific adsorption of proteins is minimized. Finally, elution of the specifically adsorbed proteins is greatly facilitated if such elution is to be performed by an exchange reaction which utilizes buffers containing specific competitive ligands.

DETAILED DESCRIPTION OF THE INVENTION

In order to further illustrate the present invention and the advantages thereof, the following specific examples pertaining to the preparation and properties of four different polyfunctional agarose derivatives are given, it being understood that the same are intended only as illustrative, and in no wise limitative. These derivatives have been found useful in the isolation and purification of various ligands, proteins, hormones, insulin receptors, and cholera toxin. The macromolecules used as polyfunctional spacer arms comprise [a] poly-L-lysine, average molecular weight 160,000 (Schwars—Mann); [b] poly(L-lysyl-DL-alanine), average molecular weight 37,500 (Miles), this is a branched chain copolymer of poly-L-lysine (backbone) and poly-DL-alanine (side chains) and the lysine to alanine ratio is 1:15; [c] native albumin (Bovine albumin, grade A (Pentex), and [d] denatured albumin, urea-denatured bovine albumin, grade A (Pentex).

POLY(L-LYSYL-DL-ALANINE)-AGAROSE AND POLY-L-LYSINE-AGAROSE

The branched-chain copolymer of L-lysine (backbone) and DL-alanine (side chains) was coupled to agarose by the CNBr activation method described at Axen et al, *Nature* 214, 1302 (1967). Compare also U.S. Pat. No. 3,947,352, supra. An aqueous suspension of 100 ml of packed agarose, in a total volume of 200 ml, was activated with 30 g of finely divided CNBr. The activated agarose cake was immediately added to a solution containing 150 mg of the poly(L-lysyl-DL-alanine) copolymer in 75 ml of 0.2 M NaICO$_3$ at pH 9; the polymer was dissolved in 5 ml of water and added to 70 ml of NaNCO$_3$ buffer. The coupling reaction was carried out by gentle agitation on a mechanical shaker at 4° for 15 hours, and for an additional 6 hours at room temperature. The substituted agarose was filtered through a coarse sintered-glass funnel and washed on the funnel without suction with one liter of 1 N NaCl over 30-60 minutes. The gel was incubated in 100 ml of 1 N glycine at pH 9 for 4 hours at 24° to mask any remaining activated agarose groups.

The agarose was washed again without suction with 2 liters of 1 N NaCl over 2-3 hours and with 1 liter of water. The substitution of the copolymer on the agarose was 1.2 mg per milliliter of packed gel as judged by the recovery of unreacted polymer in the filtrates. Poly-L-lysine-agarose was prepared utilizing the same procedure.

ALBUMIN-AGAROSE AND DENATURED ALBUMIN-AGAROSE

Albumin was coupled to CNBr-activated agarose in the presence of a high concentration of urea to promote the coupling of this protein in its unfolded state, thus increasing the likelihood of multipoint attachment of the protein to the solid support. The presence of high concentration of urea did not significantly interfere with the coupling reaction. One hundred milliliters of agarose, activated with 30 g of CNBr, was treated with 400 mg of bovine serum albumin (Pentex) dissolved in 100 ml of 0.2 N NaNCO$_3$ at pH 9, containing 10 M urea. After shaking gently for 15 hours at 4°, followed by reaction for 6 hours at 24°, the adsorbent was washed at 24° with 1 liter of 1 M NaCl (30-60 minutes) and incubated at 24° in 100 ml of 1 M lysine at pH 9, for 4 hours. The albumin-agarose was washed again with 2 liters of 1 M NaCl (2-3 hours) and 1 liter of water. The substitution of albumin, as judged by recovery in the filtrates, is 2.4 mg per milliliter of packed gel. Native albumin was coupled to agarose (agarose-albumin) as immediately above described for denatured albumin, except that the albumin was dissolved in 0.2 N NaNCO$_3$ at pH 9 in the absence of urea. The substitution of albumin was 3.5 mg per milliliter of gel.

THE USE OF MACROMOLECULAR POLYSACCHARIDE DERIVATIVES

Polysaccharide, e.g., agarose, derivatives containing the subject polyfunctional macromolecules according to the invention may be used for coupling ligands containing carboxyl or amino groups. For example, the primary amino groups of such polysaccharide derivatives are readily converted to contain a carboxylic acid function by reaction with succinic anhydride. The macromolecular derivatives containing amino or carboxyl groups can be derivatized in the several ways well known in the art. It may be especially advantageous to use amino acid polymers consisting entirely of D-stereo isomers, since such polymers would be expected to be resistant to hydrolysis by proteases present in crude tissue preparation. More especially with respect to the aforesaid derivatization, it will be appreciated that, e.g., agarose-poly(L-lysyl-DL-alanine) bearing endstanding $\alpha$—NH$_2$ groups is well adapted to couple carboxyl groups containing ligands with carbodiimide reagent. Moreover, these endstanding $\alpha$—NH$_2$ can readily be converted to endstanding —COOH groups by succinylation according to the known procedures, for coupling amino groups containing ligands, also with a carbodiimide reagent. Similarly, endstanding

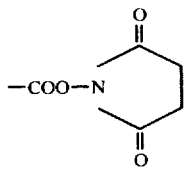

groups are fashioned by esterifying the —COOH derivatives with N-hydroxysuccinimide and a carbodiimide, again according to the known procedures, which succinimides are employed to couple proteins, amino acids and other amino-ligands under mild conditions. A protein [or polypeptide] is coupled to, e.g., agarose, by this technique, preferably through the α—NH₂ moieties thereof. An endstanding hydrazide is prepared from the α—NH₂ derivative by reaction of 2-bromoethyl acetate, followed by hydrazinolysis of the acetates. Such derivatives are useful for coupling amino-ligands [including proteins and polypeptides] via acyl azide formation. Ligands containing carboxyl groups can be coupled thereto with carbodiimide reagent. Ligands bearing aldehydic functions are readily coupled with the use of sodium cyanoborohydride (see U.S. Pat. No. 3,947,352, supra. And endstanding p-aminophenyl groups, for coupling a protein [or polypeptide] through a histidine or tyrosine residue by diazotization are prepared by reacting p-nitrobenzoylazide with the α—NH₂ derivative, followed by reduction with sodium dithionite.

The agarose-albumin [in nature or denatured form] derivatives are employed in the same techniques noted in the preceding paragraph.

All of the foregoing techniques for coupling ligands, proteins, hormones, and the like, to the subject polyfunctional polysaccharide adsorbents have been previously described. Compare those literature references, supra, hereby expressly incorporated by reference and relied upon, and the U.S. Pat. No. 3,947,352. See also Sica et al *J. Biol. Chem.*, 248, No. 18, 6543 (1973); Cuatrecasas et al, *Biochemistry*, 12, No. 21, 4253 (1973); Cuatrecasas et al, *Biochemistry* 11, No. 12, 2291 (1972); *Science*, 179, 1142 (1973); Sanderson et al, *Immunology*, 20, 1061 (1971); Lamed et al, *Biochimica et Biophysics Acts* 304, 231 (1973), likewise expressly incorporated by reference and relied upon. Various biospecific adsorbents tested further comprise insulin-, glucagon-, ganglioside-, estrogens- and renin inhibitor peptides containing agarose derivatives.

COUPLING LIGANDS TO POLYFUNCTIONAL ADSORBENTS

17β-Estradiol 17-Hemisuccinyl-Poly(L-lysyl)-DL-alanine)-Agarose.

The succinylated estradiol derivative was coupled to the polyamino acid-agarose derivative with a water-soluble carbodiimide by the procedures of Cuatrecasas, *J. Biol. Chem.*, 245, supra. Poly(L-lysyl-DL-alanine)-agarose (10 ml) was suspended in 10 ml of 70% (v/v) aqueous dioxane containing 10 mg (27 µmoles) of 17β-estradiol 17-hemisuccinate. Two 50 mg portions of 1-ethyl-3-(3-dimethylaminopropyl)carbodiimide were added 4 hours apart to the gently stirred suspension (at 24°). After 15 hours at 24° the substituted agarose was filtered on a Buchner funnel and washed at 24° with the following solvents: 500 ml of dioxane (30 min.), 5 liters of 80% (v/v) methanol (3 days), and 500 ml of water (10 min.). The substitution of 17β-estradiol was 2.5 µmoles per ml of packed gel. 17β-estradiol 17-hemisuccinate was also coupled to poly(L-lysine)-agarose by the same procedure. The corresponding derivative contains 1.5 µmoles of estradiol per ml of gel.

17β-Estradiol 17-Hemisuccinyl-Albumin-Agarose

The coupling reaction and washing procedures were carried out using albumin-agarose (or denatured albumin-agarose) as described for the preparation of the above derivatives. The substitution of the ligand was 2.6 µmoles per ml.

ESTRADIOL ADSORBENTS CONTAINING MACROMOLECULAR ARMS

Agarose adsorbents containing macromolecules (e.g., proteins or polyamino acid polymers) to which estradiol derivatives are covalently attached have proven most useful in the purification of estrogen receptors. Certain features of these adsorbents are especially advantageous in affinity chromatography. In such derivatives the ligand is separated from the matrix backbone by large distance [an average of 150 Å in A-PLL-Ala-Succ-E],* and it is possible that the microenvironment at the surface of the macromolecule is more favorable than that which exists at the immediate surface of the bead. Furthermore, it is possible with these derivatives to achieve a very high degree of ligand substitution (2 to 3 µmoles per ml of packed gel).

*17β-estradiol 17-hemisuccinyl-poly(L-lysyl-DL-alanine)-agarose

For the reasons the estradiol derivatives of such adsorbents can be so effective that the derivative shows strong and selective adsorptive properties even when it is very substantially diluted with unsubstituted agarose. Small (1 ml) columns containing 100-fold diluted samples of the four macromolecular estradiol derivatives of agarose tested can still selectively extract a significant portion of the estradiol receptor of 10 ml samples of uterine supernatant. It is notable that under such circumstances the total amount of selective adsorbent present in the column is equivalent to only about 10 µl of gel. Since this represents a very small number of beads, and these are substantially diluted, it is surprising that the diffusion limitations which these conditions should pose during chromatography do not impede the formation of significant quantities of gel-bound hormone-receptor complexes. The most effective adsorbent appears to be A-Alb-Succ-E;* the 100-fold diluted gel of this derivative can extract 40% of the receptor present in a 10 ml sample of uterine supernatant. In none of the column effluents can significant quantities of free estradiol or estradiol-receptor complexes be detected. With slower column flow rates these columns can be even more effective. For example, a 1 ml column containing a 20-fold diluted sample of A-PLL-Ala-Succ-E can extract between 70 and 90% of the receptor activity present in a 10 ml sample of uterine supernatant when the flow rate is decreased to 2 ml per hour (at 4°).

*17β-estradiol 17-hemisuccinyl-albumin-agarose

On the basis of these experiments, further large scale experiments were performed with agarose derivatives which were appropriately diluted with unsubstituted agarose. Such diluted adsorbents exhibit the special advantage of containing relatively low amounts of hormone, thus decreasing the likelihood of complications which can result from the release of free hormone during chromatography. Furthermore, the low total content of hormone facilitates the subsequent elution of the adsorbed receptor from the gel by the use of estradiol-containing solutions. Decreasing the toal quantity of substituted polymer and ligand also decreases the amount of material on the gel which can potentially act to adsorb non-receptor proteins by nonspecific interactions. The possibility of achieving a greater degree of purification is thus enhanced.

Experiments were performed to estimate the affinity of the estradiol receptor for the macromolecular agarose-estradiol derivatives to compare the relative affinities of the various derivatives. The adsorbents are incubated in suspension with varying concentrations of [$^3$H]estradiol and with the uterine supernatant, and the data were plotted in reciprocal plots to estimate the comparative affinities toward the estradiol receptor. The dissociation constant of free 17$\beta$-estradiol 17-hemisuccinate is estimated to be about $7 \times 10^{-7}$ M. Attachment of this hormone is diaminodipropylamino-agarose results in a 13-fold fall in affinity ($K_i$ about $1.4 \times 10^{-6}$ M); if the macromolecule is the branched chain copolymer of poly(L-lysine-alanine), the affinity decreases by about 4-fold ($K_i$ about $3 \times 10^{-6}$ M). It is of interest that the albumin derivative, which has a better affinity for the receptor than the amino acid copolymer derivative, is also more effective in column experiments, even when the amount of ligand substitution on the two adsorbents is approximately equal.

The washing procedures used to remove the non-covalently bound estradiol from these derivatives is greatly facilitated by diluting the adsorbents before washing. Columns containing 15 to 20 ml of packed gel (diluted 1:20) of each of the four macromolecular derivatives can be washed quite adequately by the application of 500 to 1000 ml of 80% methanol over a period of 6 to 8 hours at 24°. After this washing procedure a sample (1 ml of gel) of A-Alb-Succ-E previously diluted 25-fold with unsubstituted agarose can extract 80% of the cytosol receptor of a 6 ml sample without evidence of the existence of free estradiol or estradiol-receptor complexes in the medium. Similar results are obtained with A-PLL-Ala-Succ-E.

17$\beta$-Estradiol 17-Hemisuccinyl-Albumin-Agarose

A large scale purification experiment was performed with a column containing 3 ml of A-Alb-Succ-E diluted 1:25 with unsubstituted agarose. About 65% of the estradiol-binding activity of a 60 ml (NH$_4$)$_2$SO$_4$ sample obtained from 600 ml of crude uterine supernatant was adsorbed to this column. Elution is achieved by using the basic procedures. About 22% of the activity which binds to the column can be recovered by the elution procedure, although the over-all recovery of the starting (ammonium sulfate sample) activity is only 8%. The purification achieved in this experiment is at least 4400-fold.

17$\beta$-Estradiol 17-Hemisuccinyl-Poly(L-lysyl-DL-alanine)-Agarose

A large scale experiment was performed with a small column containing a 20-fold diluted sample of A-PLL-Ala-Succ-E. The column extracts the major portion of the estradiol-binding activity of the ammonium sulfate preparation (82 ml) which is applied to the column. More than 45% of the activity bound to the adsorbent can be eluted by the estradiol competitive exchange reaction performed in batchwise form. In four separate column experiments, the columns extract from 70 to 83% of the estradiol-binding activity applied to the column, and 46 to 94% of this activity can be subsequently recovered. The total recovery of receptor protein, starting from the crude uterine supernatant, varies from 30 to 73%. In these experiments the receptor protein is purified by a factor of from 8,500 to nearly 13,000. In the experiments described, the estimates of the purification achieved are based on a maximum estimate of the amount of protein since no protein was detectable in the eluates in these experiments. In other large scale experiments, where the protein content of the eluted material was determined by amino acid analysis of acid hydrolysates, purification in excess of 100,000-fold has been achieved. Sica et al, supra.

PREPARATION OF HYDRAZIDO DERIVATIVES OF AGAROSE

Hydrazido derivatives of agarose, prepared by the reaction of succinic dihydrazide with sodium periodate-oxidized agarose have been described in U.S. Pat. No. 3,947,352.

The hydrazido derivatives of agarose gels which contain the subject macromolecular arms offer many special advantages over the succinic dihydrazido-agarose. Depending on the size and molecular weight of the polyfunctional macromolecule used, the ligand or protein to be coupled can be very conveniently separated from the agarose matrix by distances of varying length; approximately 150 Å with poly(L-lysyl-DL-alanine) of 37,500 daltons.

Poly-(L-lysyl-DL-alanyl-hydrazido)-Agarose

The agarose derivative of poly-(L-lysyl-DL-alanine), prepared by the NaIO$_4$ method, was converted to a poly-N-carboxymethyl ester by reaction with bromoacetic ester [Eastman]. The polyester was then converted to the hydrazide form by treatment with aqueous hydrazine.

Poly-(L-lysyl-DL-alanine)-agarose, 10 ml, was suspended in 10 ml of saturated sodium borate and 1.5 ml of 2-bromoacetic ester was added. The suspension was gently shaken overnight in a tightly closed polyethylene bottle at 24°. The agarose derivative was washed over a sintered-glass funnel with 100 ml of water and 100 ml of dioxane. The agarose coke was suspended in 10 ml of 5 N aqueous hydrazine solution. The suspension, after shaking gently for an additional 8–10 hours at 24°, was filtered and washed extensively with 1 N NaCl solution until the TWBS test for hydrazine in the wash was negative. The reaction was performed in a well-ventilated hood.

Coupling Ligands to Hydrazido-Agarose

The coupling of amino group-containing ligands and proteins to hydrazido-agarose was performed by essentially the same method as described in Inman et al., *Biochemistry*, 8, 4074 (1969). Because of the very limited stability of the intermediate acyl azide formed by nitrous acid, the time and temperature of the activation and coupling reactions was carefully controlled.

Poly-(L-lysyl-DL-alanyl-hydrazido)-agarose, 10 ml. was suspended in 8 ml of water, and 2 ml of 1 M HCl were added. The suspension was cooled in an ice bath for 30 minutes and, while stirring, 2 ml of an ice-cold solution of 1 N NaNO$_2$ was added dropwise over 1 minute periods. The suspension was stirred for an additional 2–3 minutes, then rapidly (1–2 minutes) filtered with suction on a coarse sintered-glass funnel (previously cooled) and washed with 20–30 ml of cold 5 mN HCl. The outlet of the sintered-glass funnel was covered with Parafilm, and a 50 mN solution of [$^{14}$C]-L-alanine (0.1 μCi/μmole) in a 0.2 M sodium bicarbonate at pH 8, was added while being stirred with a glass rod. The suspension was transferred to a polyethylene vial and shaken gently for 15 hours at 4°. The substituted agarose was washed extensively with 1 M NaCl. Substitution of [$^{14}$C]alanine was about 1 μmole per milliliter of agarose.

PREPARATION OF HYDRAZIDO-ALBUMIN

Another approach to the preparation of hydrazido macromolecular derivatives is to synthesize hydrazido-albumin, which can then be coupled to agarose, stored in buffer, and activated for use when needed. Hydrazido-albumin is prepared by esterifying the aspartate and glutamate carboxyl groups with methanol, HCl being used as the catalyst. The esterified albumin is then treated with hydrazine to convert the esters to acyl hydrazides. The hydrazido-albumin is coupled to agarose in denaturing solvents (urea or guanidine HCl) with CNBr. These agarose beads are then activated by reaction with dilute nitrous acid to convert the hydrazido groups to acyl azide groups. The latter can react rapidly with amines to form amides.

Hydrazido-albumin is prepared by dissolving 5 g of bovine albumin in 100 ml of anhydrous methanol and adding 72 mg (20 mmoles) of anhydrous HCl gas. The solution is stirred overnight at room temperature. A white precipitate forms which is collected by filtration, washed once with ethanol, and suspended in 100 ml of anhydrous ethanol. Hydrazine (3.2 g, 300 moles) is added and allowed to react for 20 hours at room temperature while the suspension is stirred. The solvents are removed on a vacuum evaporator, and the residue is suspended in ethanol and dried again. The residue is dissolved in 6 M guanidine HCl to give a final concentration of 10 mg/ml. One volume of the protein solution is added to 1 volume of 0.2 M NaHCO$_3$ at pH 9.5, and allowed to react with 2 volumes of CNBr-activated agarose by the buffer activation method. The hydrazido-albumin agarose is activated with nitrous acid as described above. Preliminary studies with insulin as a test ligand indicate that the coupling efficiency of this macromolecular gel is about 10% of that of CNBr-activated agarose.

Other suitable polyfunctional macromolecules which can be utilized according to the present invention include polyglutamic acid, polyaspartic acid, polyornithine and various copolymers thereof with amino acid comonomers copolymerizable therewith, such as alanine and glycine. Suitable derivatives of such "other" polyfunctional macromolecules too can be utilized according to the invention, for example, the hydrazides, active esters, azides and diazonium salts.

While the invention has been shown and described and pointed out with reference to certain preferred embodiments thereof, those skilled in the art will appreciate that various changes, modifications, substitutions, and omissions can be made by those skilled in the art without departing from the spirit of the invention. It is intended, therefore, that the invention be limited only by the scope of the claims which follow.

What is claimed is:

1. In a polysaccharide matrix useful as an adsorbent for affinity chromatography techniques, the improvement which comprises a plurality of polyfunctional, water-soluble macromolecular spacers individually covalently bonded to the backbone of said polysaccharide matrix in direct multipoint covalent attachment thereto, the said polyfunctional macromolecular spacers being selected from the group consisting of (1) poly-L-lysine, (2) the graft copolymer, poly(L-lysyl-DL-alanine), (3) native albumin and (4) denatured albumin and the end-standing functional groups of said polyfunctional macromolecular spacers being essentially sterically unhindered with respect to said polysaccharide matrix.

2. The polysaccharide matrix as defined by claim 1, wherein the polyfunctional macromolecule is poly(L-lysyl-DL-alanine), a graft copolymer of poly-L-lysine (backbone) and poly-DL-alanine (side chains).

3. The polysaccharide matrix as defined by claim 2, wherein the poly(L-lysyl-DL-alanine) has an average molecular weight of about 37,500 and a lysine to alanine ratio of about 1:15.

4. The polysaccharide matrix as defined by claim 1, wherein the polyfunctional macromolecule is poly-L-lysine.

5. The polysaccharide matrix as defined by claim 4, wherein the poly-L-lysine has an average molecular weight of about 160,000.

6. The polysaccharide matrix as defined by claim 1, wherein the polyfunctional macromolecule is native albumin.

7. The polysaccharide matrix as defined in claim 6, wherein the native albumin is bovine albumin.

8. The polysaccharide matrix as defined by claim 1, wherein the polyfunctional macromolecule is denatured albumin.

9. The polysaccharide matrix as defined by claim 8, wherein the denatured albumin is urea-denatured bovine albumin.

10. The polysaccharide matrix as defined by claim 1, wherein the polysaccharide is selected from the group consisting of cellulose, starch, cross-linked dextran, and agarose.

11. The polysaccharide matrix as defined by claim 1, wherein the said polysaccharide-polyfunctional macromolecular complex is diluted with an unsubstituted polysaccharide gel.

12. The polysaccharide matrix as defined by claim 11, wherein the said dilution is about 200- to 600-fold.

13. In a method for the affinity chromatography by technique of coupling ligands, proteins, hormones, nucleotides and nucleosides to a polysaccharide matrix, the improvement which comprises coupling said biologically active molecules to the polysaccharide matrix as defined by claim 1.

14. The method as defined by claim 13, wherein the molecule coupled to the said polysaccharide matrix is selected from the group consisting of ligands bearing an amino function and ligands bearing a carboxyl function.

15. The method as defined by claim 14, wherein the ligand is separated from the polysaccharide matrix by a distance in the order of 150 Å.

16. The product of the method as defined by claim 13.

17. The product of the method as defined by claim 14.

18. In an affinity chromatography column comprising an insoluble, solid polysaccharide adsorbent, the improvement which comprises, as the adsorbent thereof, the polysaccharide matrix as defined by claim 1.

19. In a polysaccharide matrix useful as an adsorbent for affinity chromatography techniques, the improvement which comprises a plurality of polyfunctional, water-soluble macromolecule spacers individually covalently bonded to the backbone of said polysaccharide matrix in direct multipoint covalent attachment thereto, the polyfunctional macromolecule comprising endstanding functional groups, and the endstanding functional groups of said polyfunctional macromolecule being essentially sterically unhindered with respect to said polysaccharide matrix.

20. The polysaccharide matrix as defined by claim 19, wherein the polyfunctional macromolecule is a polyamino macromolecule.

21. The polysaccharide matrix as defined by claim 19, wherein the endstanding functional groups of said polyfunctional macromolecule comprise a succinyl moiety.

22. The polysaccharide matrix as defined by claim 19, wherein the endstanding functional groups of said polyfunctional macromolecule comprise a hydrazide moiety.

23. The polysaccharide matrix as defined by claim 19, wherein the endstanding functional groups of said polyfunctional macromolecule comprises a p-aminophenyl moiety.

24. The polysaccharide matrix as defined by claim 19, wherein the endstanding functional groups of said polyfunctional macromolecule comprise a

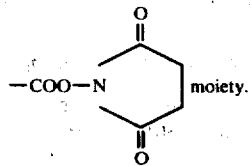
moiety.

25. The polysaccharide matrix as defined by claim 19, wherein the endstanding functional groups of said polyfunctional macromolecule comprise a moiety selected from the group consisting of α of ξ $NH_2$, carboxyl, azide, ester and diazonium salt.

* * * * *